United States Patent [19]
Ko

[11] Patent Number: 5,866,424
[45] Date of Patent: Feb. 2, 1999

[54] STABLE LIQUID UROBILINOGEN CONTROL COMPOSITION

[75] Inventor: Benjamin Ko, Winchester, Va.

[73] Assignee: Bayer Corporation, Elkhart, Ind.

[21] Appl. No.: 500,474

[22] Filed: Jul. 10, 1995

[51] Int. Cl.$^6$ .................................................. G01N 37/00
[52] U.S. Cl. ................................ 436/8; 436/12; 514/422
[58] Field of Search ............................ 514/422; 436/12, 436/8

[56] References Cited

FOREIGN PATENT DOCUMENTS 62-175666  8/1987  Japan .

OTHER PUBLICATIONS

Kotal et al., Clinica Chemica Acta, 202, pp. 1–10, Oct. 1991.
Fetter et al., American Journal of Medical Technology 47(9), Sep. 1981.
Rupe et al., Clinical Chemistry 27(8), pp. 1385–1387, Aug. 1981.
Fischer et al., Hoppe–Seyler's Zeitschrift F. Physiol. Chemie CXXVII pp. 293–316 (translation), 1924.
Watson et al, Biochemical Medicine 2, 484–508, 1969.
Petryka "Variations in Hydrogenation of Bile Pigments . . . ", Annals New York Acaemy of Sciences, 206, pp. 701–710 (1973) Translation of JP62175666 (Hisatsu et al.).
Gray et al. "The Chemistry of the Bile Pigments . . . " J.Chem. Soc. 2268 (1961) pp. 2268–2285.
Levy et al. "Renal Excretion of Urobilinogen in the Dot", CA Abstract 69:104478 of J. Clin. Invest. (1968) pp. 2117–2124 (47(9) (1968).
Fetter et al., Biochemical Medicine, pp. 484–508, 1969.

*Primary Examiner*—Jeffrey C. Mullis
*Attorney, Agent, or Firm*—Roger N. Coe

[57] ABSTRACT

The present invention addresses the need to ensure that clinical tests for urobilinogen in urine are properly working. The invention specifically provides a novel liquid urobilinogen composition which remains stable in liquid form for eighteen months and a method for making the same.

4 Claims, No Drawings

STABLE LIQUID UROBILINOGEN CONTROL COMPOSITION

FIELD OF THE INVENTION

The present invention relates to a liquid urinalysis control solution for urobilinogen. The invention more particularly concerns a stable liquid urobilinogen composition which can be used to ensure that test compositions and devices for urobilinogen detection are working properly.

BACKGROUND OF THE INVENTION

In clinical testing and diagnostics, many reagent strips used to analyze urine contain tests for urobilinogen. Urobilinogen is a reduction product of bilirubin which itself is formed from the degradation of the red blood cells. Normally, there is little or no urobilinogen excreted into the urine unless a pathological condition exists.

The presence of abnormally high levels of urobilinogen in a patient's urine is possibly indicative of hepatic diseases, hemolytic diseases and biliary obstruction. In particular, the determination of abnormally high urobilinogen levels is particularly useful for detecting the early stages of hepatitis. The commercially available Multistix® reagent strips of Bayer Corporation, Elkhart, Ind., is a typical example of such reagent strips. The reagent test pad condenses urobilinogen with diethylaminobenzaldehyde under acidic conditions to produce the diethylaminobenzylidenyl urobilinogen responsible for the optical signal. As part of normal quality control, the clinician must be assured that the urobilinogen test is working properly by employing a positive control for the test which mimics the urobilinogen material in a patient sample. A specified amount of urobilinogen is thus added to synthetic or fresh urine that is free of endogenous urobilinogen to produce a control solution. This control solution is then used to monitor the accuracy and precision of urine urobilinogen tests.

Traditionally, liquid urobilinogen is synthesized artificially by reducing bilirubin using a catalyst such as sodium amalgam, vanadium or platinum. There have, however, been problems with these traditional methods of synthesis. Sodium amalgam, for instance, is unstable and causes environmental pollution through mercury contamination. Vanadium and platinum are readily oxidizable, expensive and require special equipment when used as catalysts for bilirubin reduction.

Alternately, Raney nickel, copper or iron can be used to reduce bilirubin to urobilinogen. Raney catalysts are powdered metals of nickel, copper, or iron prepared from an alloy of the metal and aluminum by dissolving the aluminum in an alkali solution. Urobilinogen produced by utilizing a Raney catalyst requires lyophilization to ensure extended stability. Specifically, 10% or more of liquid urobilinogen produced by reduction with a Raney catalyst degrades significantly in one day even under refrigeration. Lyophilization is an extra step that adds additional costs and labor to urobilinogen production. Lyophilization also forces the clinician to expend additional time reconstituting the lyophilized powder. Such reconstitution may sacrifice precision quantification of urobilinogen content when the product is reconstituted. Furthermore, the protocol involving Raney catalysts is relatively tedious to perform because the reduction reaction must be performed at 10° C. or lower to effect a reaction.

Given the limitations of the existing methods of producing both lyophilized and liquid urobilinogen and the inherent problems associated with a product which must be stored in lyophilized form, there is a clear need for a method of producing a stable liquid urobilinogen composition which can be produced safely, easily and inexpensively.

SUMMARY OF THE INVENTION

The present invention provides a stable liquid urobilinogen composition and method of synthesis. This composition can be used as a positive control solution to monitor the accuracy of chemical compositions and test devices utilized to detect urobilinogen in urine.

The composition of the present invention specifically provides a liquid urobilinogen composition that is stable in liquid form for eighteen months. The composition is synthesized by the reduction of bilirubin by hydrogen with palladium on activated carbon as a catalyst. An optimal concentration of palladium consists of approximately 10% palladium on activated carbon by weight.

A further aspect of the present invention provides a method of producing a urobilinogen composition that is stable in liquid form. The method involves reducing bilirubin by hydrogen with palladium and then storing the resulting composition in liquid form under an inert gas. A preferred metal reduction catalyst is 10% palladium on activated carbon by weight. A preferred pressure under which bilirubin is reduced with hydrogen is 60 pounds per square inch and a preferred temperature of hydrogenation is room temperature. Finally, a preferred inert gas under which the liquid urobilinogen is stored is argon or nitrogen.

The invention further provides a method of ensuring that a clinical diagnostic urobilinogen test is working to accurately detect urobilinogen in urine. This method involves utilizing the urobilinogen composition of this invention as a positive control for such clinical tests. The composition of the present invention can be used alone in synthetic or fresh urine to provide quality assurance that a urobilinogen test is working properly. Alternatively, the composition can be incorporated into a more comprehensive control solution containing a variety of substances found in urine. Such a comprehensive control solution can be used to ensure that tests for multiple analytes, including urobilinogen, are properly working.

DESCRIPTION OF THE PREFERRED EMBODIMENT

The present invention provides a novel liquid urobilinogen composition for use as a positive control solution to monitor the accuracy and precision of urine urobilinogen tests. More specifically, the invention provides a composition and method of making the same which produces a urobilinogen solution safely, easily and inexpensively and which stays stable in liquid form for at least eighteen months.

Urobilinogen is a reduction product of bilirubin. It is formed in vivo through the reduction of bilirubin by enteric bacteria. Many clinical tests seek to measure urobilinogen in a patient's urine because its presence is likely indicative of a pathological condition. This invention provides a positive control for such urobilinogen tests. Positive control means that the present invention mimics urobilinogen in urine so that a clinician or patient can ensure that a urobilinogen test is working by using the urobilinogen test with the control.

The urobilinogen composition of the present invention is produced by reducing bilirubin by hydrogen with the addition of palladium as a catalyst. Reduction means the addition of electrons to a compound. A preferred reduction reaction using 10% palladium on activated carbon by weight as a catalyst.

A preferred pressure and temperature of hydrogenation is sixty pounds per square inch (psi) pressure at room temperature.

The urobilinogen composition of this invention, unlike those produced by the reduction of bilirubin with Raney catalysts, remains stable in liquid form for at least 18 months. It is believed that the hydrogenation under pressure stabilizes the composition in liquid form. Example 1 describes in detail the protocol whereby the urobilinogen composition of the present invention is produced.

The urobilinogen composition of the present invention can be used as a positive control to ensure that clinical diagnostic urobilinogen tests are properly working. For example, to determine whether a reagent test strip such as the Multistix® reagent strip is properly working to detect urobilinogen, a clinician or patient simply dips the test strip directly into the urobilinogen composition of the present invention which is diluted in fresh human or synthetic urine. If the urobilinogen indicator color block on the reagent strip turns the appropriate color in response to the urobilinogen composition, one can be ensured that the reagent test strip is properly functioning.

Alternatively, the urobilinogen composition of the present invention can be incorporated into a comprehensive multiple control system such as Bayer's bi-level urinalysis control solutions. In the bi-level control system, one solution, designated Level 1, mimics the analytes found in normal urine and a second solution, designated Level 2, mimics the analytes found in abnormal urine. The urobilinogen composition of the instant invention is incorporated into the Level 2 liquid control solution for abnormal urine.

The control solutions are used to monitor the precision of the test strips to ensure that the chemical reagents of each test area of the strips are functioning properly prior to use on a patient sample. The control solutions can be used daily or weekly according to a laboratory established quality control policy. Level 1 acts as a negative control. That is, the Level 1 control solution ensures that test strips from a particular lot or package will not create a false positive color change for certain analytes found only in abnormal urine upon exposure to normal urine. Level 2 acts as a positive control. Thus, it ensures that the reagent strips from a particular lot will properly detect analytes which may be found in a patient sample of abnormal urine.

A user of the Level 1 and 2 control solutions tests a single reagent strip in the Level 1 control solution and a single strip in the Level 2 control solution containing urobilinogen to ensure that a particular lot of strips are properly working.

Level 1 control is a liquid stable, synthetic matrix plus dyes to mimic the color of the urine. It has a clean appearance, pale yellow color with pH adjusted to 6 and the specific gravity approximately 1.025. Level 1 control is negative for glucose, bilirubin, ketones, hemoglobin, protein, nitrite, leukocyte esterase and normal for urobilinogen on Multistix® 10 SG reagent strips. The osmolality is approximately 550 mOsm, sodium between 110 and 140 mmol/L (millimoles perliter), potassium between 80 and 100 mmol/L (millimoles perliter) and ascorbic acid less than 10 mg/dL (milligram perdeciliter).

Level 2 control is a liquid stable, synthetic matrix, formulated with Hepes buffered salt with pH adjusted to 8 and specific gravity approximately 1.010. It has a clear appearance, bright yellow-amber color. Level 2 control is positive on Ames Multistix 10 SG reagent strips for glucose, bilirubin, ketones, hemoglobin, protein, urobilinogen, nitrite and leukocyte esterase. The osmolality is approximately 300 mOsm, sodium between 90 and 110 mmol/L, potassium between 20 and 40 mmol/L and ascorbic acid will be greater than 10 mg/dL.

The urobilinogen composition of the present invention formulated as described in Example 1 is stable for 18 months when stored at 5° C. in liquid form. The composition was tested for stability alone and also when incorporated into the urobilinogen comprehensive urine control solution. Stability testing is performed by periodically dipping Multistix® reagent test strips into the urobilinogen containing solution to be used. The solution is considered stable if it elicits a color reaction on a test strip detectable by visual inspection within two color blocks from the expected reaction.

EXAMPLE 1

Production of Urobilinogen by Reduction of Bilirubin Using Palladium on Activated Carbon 5.0 g (grams) Bilirubin, 5.0 g Palladium on Carbon (preferably 10% powder by weight) and 200 mL (milliliters) of 0.1N aqueous NaOH was added to a 250 mL Parr bottle. The bottle was protected from light with aluminum foil, wrapped with a steel jacket, capped and connected to a hydrogenator. The system was then evacuated a few times and filled with hydrogen to a pressure of 60 psi. When the hydrogen uptake ceased (not lower than 35 psi), the system was stopped and refilled back to 60 psi. The hydrogenation was allowed to continue (not less than 52 psi) for no less than 8 hours (preferably overnight). The black reaction mixture was filtered through 15–30 g of Celite 545 on a Whatman filter in a Buchner funnel. The Celite pad was then washed with 50–80 mL of water to bring the final concentration of urobilinogen to approximately 2000 mg/dL. The solution was again filtered using 0.22–0.45 micron filters into an amber bottle. Inert gas (Nitrogen/Argon) was used to purge air and oxygen from the bottle for 10 minutes. The bottle was stored at 20° C. in order to protect urobilinogen stability for at least 18 months.

What is claimed is:

1. A method of producing a urobilinogen composition that is stable in liquid form comprising:
    a) reducing bilirubin with hydrogen utilizing palladium on activated carbon as a catalyst such that bilirubin is reduced for at least eight hours and at a pressure sufficient to allow hydrogenation to occur such that essentially all of the bilirubin is reduced to urobilinogen, and
    b) storing said urobilinogen composition under a blanket of inert gas.

2. The method of claim 1 wherein bilirubin is reduced with hydrogen at a pressure of 60 pounds per square inch at room temperature.

3. A method of ensuring that a clinical diagnostic urobilinogen test device is properly working comprising:
    utilizing the urobilinogen composition comprising a product obtained by the process of claim 1 as a positive control for said clinical diagnostic urobilinogen device.

4. A method of producing a urobilinogen composition that is stable in liquid form comprising:
    a) reducing bilirubin with hydrogen utilizing palladium on activated carbon as a catalyst such that bilirubin is reduced for at least eight hours and at a pressure of 60 pounds per square inch at room temperature; and
    b) storing said urobilinogen composition under a blanket of inert gas consisting of a mixture of nitrogen and argon.

* * * * *